United States Patent [19]

Meserol

[11] Patent Number: 5,474,528
[45] Date of Patent: Dec. 12, 1995

[54] COMBINATION CONTROLLER AND PATCH FOR THE PHOTODYNAMIC THERAPY OF DERMAL LESION

[75] Inventor: Peter M. Meserol, Montville, N.J.

[73] Assignee: Dusa Pharmaceuticals, Inc., Denville, N.J.

[21] Appl. No.: 215,273

[22] Filed: Mar. 21, 1994

[51] Int. Cl.⁶ .................................................. A61N 1/30
[52] U.S. Cl. .............................. 604/20; 607/88; 607/90
[58] Field of Search ........................ 607/88–93; 604/20; 250/497.1; 601/15, 18

[56] References Cited

U.S. PATENT DOCUMENTS

| | | | |
|---|---|---|---|
| 4,932,934 | 6/1990 | Dougherty et al. | 607/89 |
| 5,288,289 | 2/1994 | Haak et al. | 604/20 |
| 5,298,017 | 3/1994 | Theeuwes et al. | 604/20 |

FOREIGN PATENT DOCUMENTS

| | | | |
|---|---|---|---|
| 9000420 | 1/1990 | WIPO | 607/88 |

*Primary Examiner*—Lee S. Cohen
*Assistant Examiner*—Robert L. Nasser, Jr.
*Attorney, Agent, or Firm*—R. Gale Rhodes, Jr.

[57] ABSTRACT

Combination controller and patch for photodynamic therapy of a dermal lesion located at a dermal treatment site on skin including stratum corneum, the controller is optically connected to the patch and the patch includes hydrogel containing hydration agent and photopharmaceutical, the patch covers the site and the hydrogel engages and couples the hydration agent to the stratum corneum to hydrate and soften the stratum corneum to enhance its optical transmissiveness to facilitate the transmission of light therethrough and to enhance its chemical transmissiveness to facilitate the transmission therethrough of the photopharmaceutical for treatment of the dermal lesion, light delivery apparatus are included in the patch for receiving light from the controller and for delivering light through the hydrogel and the hydrated stratum corneum to the site to photoactivate the photopharmaceutical at the site to treat the dermal lesion.

9 Claims, 5 Drawing Sheets

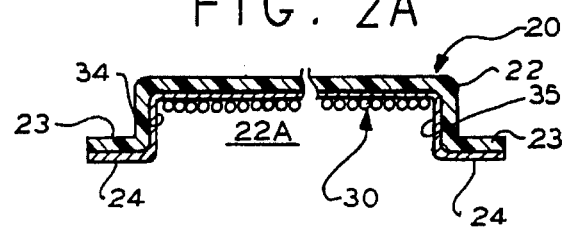
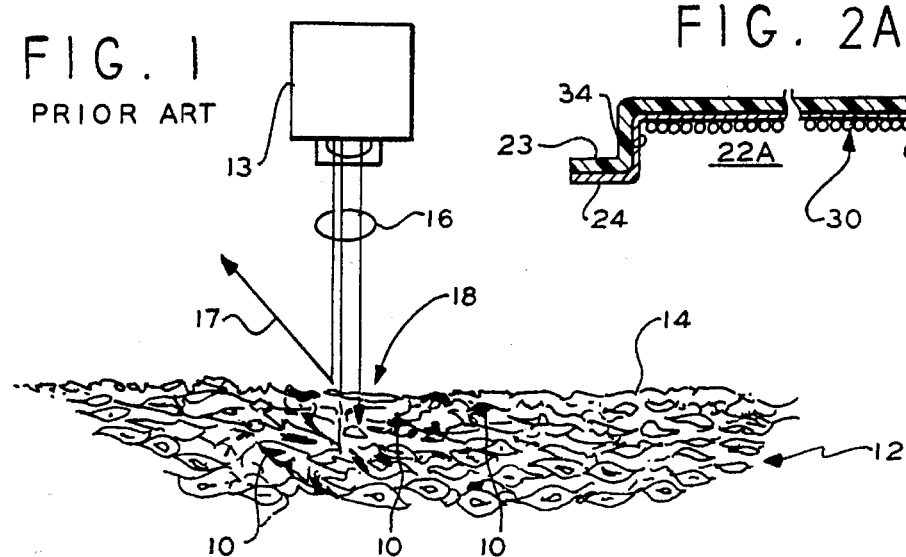
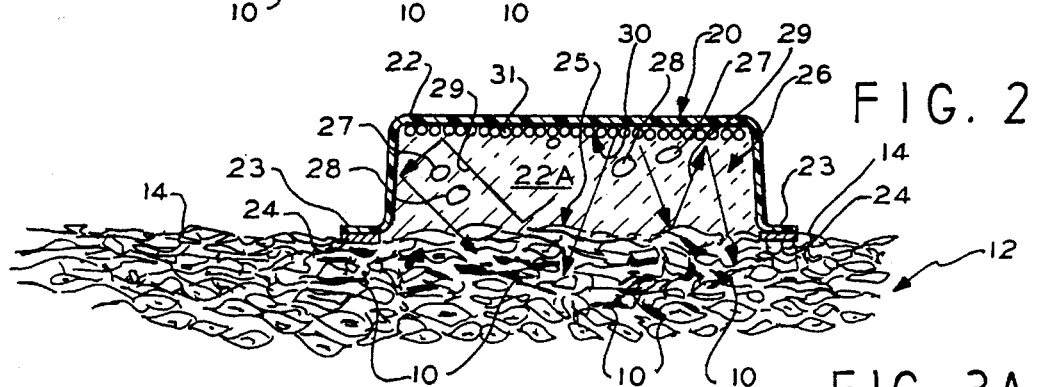
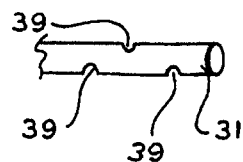
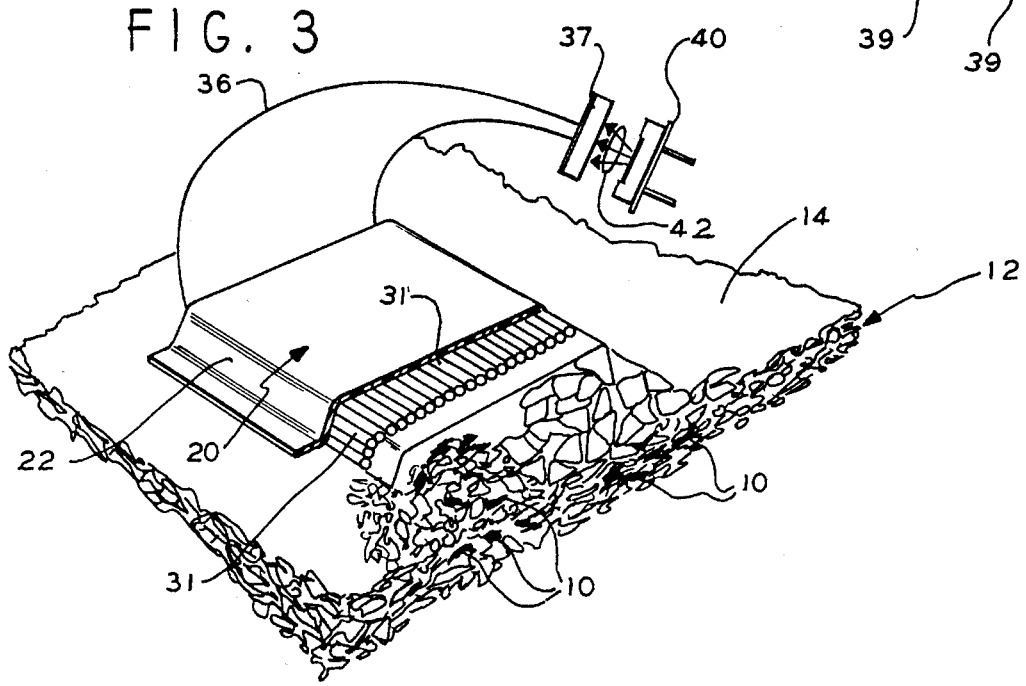

COMBINATION CONTROLLER AND PATCH FOR THE PHOTODYNAMIC THERAPY OF DERMAL LESION

BACKGROUND OF THE INVENTION

This invention relates generally to combination controller and patch for the photodynamic therapy (PDT) of dermal lesion such as for example actinic keratosis, basal carcinoma and psoriasis. More particularly, this invention relates to a portable combination controller and patch for applying photodynamic therapy to a dermal lesion using a light or photoactivated photopharmaceutical wherein the amount of photopharmaceutical activation is patient controllable for patient comfort.

Bodies, sheet or layer forms, of hydrogel or hydrogel materials, particularly transparent hydrogel or hydrogel materials, are well known in the medical field and may comprise, for example, a polyvinyl alcohol with a water matrix; some of these transparent hydrogel or hydrogel materials are castable and may be cast into intimate contact with other devices. They have been widely adapted to such applications as diagnostic electrodes (for EKG), wound care dressings, and transdermal delivery devices for systemic delivery of pharmaceutical agents. The biocompatability of this class of materials is well established for extended contact with dermal structures. Much of the prior art in medical applications for hydrogel or hydrogel materials teaches devices and methods for electrical conductivity enhancement. Critical in using hydrogel in many medical applications, such as an electrical interface, is the ability of the hydrogel to form intimate physical contact with skin or dermal structures. U.S. Pat. No. 5,143,071 issued to Keusch et al. on Sep. 1, 1992, cites an extensive list and description of prior art hydrogels suitable for this purpose, and this patent is incorporated herein by reference.

A concurrent body of prior art embraces hydrogels or hydrocolloids, as wound dressings and dressings impregnated with pharmaceutical compounds; representative of this prior art is U.S. Pat. No. 5,156,601 to Lorenze et al. Further, the work of Gombotz et al., Proc. Intl. Symp. Cont. Rel. Bioact. Mtl., Vol. 19, 1992, describes the rapid release of complex compounds from hydrogels to skin or dermal structures.

U.S. Pat. No. 5,079,262 issued to Kennedy et al. discloses a method of detection and treatment of malignant and non-malignant lesions utilizing 5-aminolevulinic acid. The acid is administered to a patient in an amount sufficient to induce synthesis of protoporphyrin IX in the lesions, followed by exposure of the treated lesions to a photoactivating light in the range 350–640 nm. The acid is taught to be administered to the patient orally, topically or by injection.

None of the prior art references teach or suggest the photodynamic therapy of dermal lesions using hydrogel as an optical, chemical or fluidic coupling agent for light and photopharmaceutical to skin. Since its first reported clinical use at the turn of the century, photodynamic therapy has been accomplished using light projected to the dermal treatment site from sources at some distance from the site. Modern photodynamic therapy (from 1978 onwards) has developed light delivery protocols using artificial sources such as tungsten halogen, or xenon arc lamps with wavelength filtration to activate photopharmaceuticals. All of the above light sources have been used in projective, field illuminating devices that flood the target treatment field or site in the treatment of superficial cutaneous lesions with light containing a wavelength designed to activate the photopharmaceutical. These references generally teach that the dosimetry of applied photodynamic therapy can be controlled and varied by varying the intensity and/or duration of the photoactivating light applied to a photopharmaceutical performing photodynamic therapy.

In the case of the tungsten and xenon-arc sources, extensive filtration of the available light flux is essential to restrict the delivered energy to appropriate wavelengths that photoactivate the photopharmaceutical in the target dermal structures. Colored glass or interference filters used with these sources transmit some portion of unwanted wavelengths, notably in the infrared region, and can cause thermal effects that may mask the effect of photoactivity with an undesirable heating effect that also preferentially damages malignant tissue. High-power surgical lasers, even when de-focussed, also can induce undesirable thermal effects. The work of Svaasland, Photochem/Photobiol. 1985, measured this effect and its impact on PDT protocols.

Dosmetry of delivered photodynamically effective light to a dermal treatment site is extremely difficult using current projective optics. Mathematical modeling of skin optics has been a slow and difficult process. Recent publications by Van Gemert et al., IEEE Trans. Biomed. Eng., Vol. 36;12, 1989, critically reviewed the prior work and presents a 4-layer model of light-dermal tissue interaction; this publication is incorporated herein by reference. Van Gemert et al. elaborates on the advantages and effectiveness of the diffusion model of light transport in tissue, which depends upon the efficient coupling of the externally applied light to the target tissue. A later publication by R. Rox Anderson, Optics of the Skin, Clinical Photomedicine, Dekker Publication, 1993, reviews the two basic processes which govern the optics or behavior of light in skin, namely, light absorption and light scattering; this publication is incorporated herein by reference.

It has been found that an efficient and practical means of establishing the diffusion conditions of light transport is to provide transparent coupling means that is in intimate contact with the skin containing dermal lesions on one surface and with the light source on its opposite surface. Under these conditions reflective losses are reduced, and delivered optical energy is much more efficiently transmitted into the target region.

The stratum corneum present at a dermal treatment site on the skin of a person is a formidable barrier to transport (transmission, penetrability or permeability) of light into the deeper structures of the skin where dermal lesions typically reside, in whole or in part. The layered plate-light corneocytes comprising the stratum corneum constitute an efficient reflective optical surface which reflects nearly all light in the visible spectrum. There is some transmission in the region of 590 to 700 nanometers. Photopharmaceuticals are formulated to be activated by light energy in this region. Penetration depth is in the region of 1–3 mm from the dry corneocyte surface. It has been discovered that the interposition of a flexible transparent hydrogel coupling layer between a monochromatic plate or sheet-formed light source and the skin surface constitutes a new and more efficient delivery of activating optical energy to target dermal lesions for photodynamic therapy; particularly where the monochromatic light source delivers light at the specific wavelength at which the photopharmaceutical is photoactivated.

There are other substantial benefits that attend the use of an intimately contactive hydrogel coupling layer. Because hydrogels are typically 60 to 90% water, hydration of the stratum corneum occurs rapidly following contact with the hydrogel sheet. This hydration has a substantial optical transparency, or optical transmissiveness, enhancing effect, allowing more light to pass through the stratum corneum. Although the mechanism of this optical transparency has not been extensively studied, it is thought to result from a reduction of the light reflectivity of the stratum corneum through softening of the corneocytes by a solvent or plasticizing action. Castable transparent hydrogels are also known to the art which may be cast into intimate physical and optical contact with, for example, a source of light.

It is well established in the literature of chemical transport through the skin that hydration can enhance the chemical transparency, transmissiveness, passage or transport of pharmaceuticals through the stratum corneum. A review of discussion of this enhanced transport under hydrated conditions is found in Ghosh et al., pharmaceutical Tech., April 1993, which publication is incorporated herein by reference.

It follows that there are two key requirements of PDT to dermal structures where the protocol requires topical application of the photopharmaceutical. Transport of the photopharmaceutical into target tissue, and subsequent light activation of the photopharmaceutical at the target tissue, these can be more efficiently accomplished using the diffusion route for both the drug and the activation optical energy.

It has been found that a hydrogel coupling layer serves the dual purpose of establishing conditions for the optical energy diffusion into skin tissue and photopharmaceutical compound diffusion or other introduction into skin tissue, by the intercellular or transcellular routes; however, it will be understood that the introduction of the photopharmaceutical from the hydrogel into the hydrated skin or through the hydrated stratum corneum, depending on the specific photopharmaceutical used, can be by the above-noted diffusion, or by absorption, or by other mechanism constituting chemical permeation or penetration of the hydrated skin or stratum corneum. A third optical advantage of a transparent transport hydrogel is that it can remain in place after PDT exposure, as a protective dressing.

In the preferred embodiment of this invention, a transparent hydrogel serves as a transport or reservoir of a hydration agent and photopharmaceutical and which hydrogel rapidly releases the photopharmaceutical to the skin tissue. For purposes of photodynamic therapy, rapid delivery is desirable. This contrasts with prior art transdermal devices for non-PDT drug delivery which seek to provide much slower release kinetics for system absorption. Further, in the present invention, the photodynamic therapy is localized to a dermal treatment site defined by a cover, container or patch covering the site where the dermal lesion is located and the light necessary to activate the photopharmaceutical is delivered only to the dermal treatment site. It is thus advantageous to rapidly deliver the light activated photopharmaceutical doses to skin tissue, and dermal lesion, and then deliver the light dose to initiate its biological activity to treat the dermal lesion.

The intimate hydrogel contact established at the skin surface of the treatment site forms both a fluid or fluidic coupling for the photopharmaceutical and an optical or optic coupling for the photoactivating light. In the case of the chemical or fluidic coupling, the water contained in the hydrogel matrix begins to solubilize the stratum corneum, hydrating this normally dry layer, and forms an avenue of exchange between the hydrogel and the dermal lesion. Hydration enhances both intracellular and transcellular pathways. Upon establishment of these pathways, transport of the photopharmaceutical to target tissue or dermal lesion commences.

The effect of hydration on fluid transport across the stratum corneum layer is substantial. Normally this structure contains 10–15% water. Hydrated stratum corneum can retain up to 50% water and the normal light diffusion coefficient of the hydrated stratum corneum can increase ten-fold.

The effect of hydration on optical coupling of light into skin tissue is also substantial, but is sustainable only with the contact of the transparent hydrogel to both the skin tissue and the light source. In the preferred embodiment a fiber optic panel comprising a plurality of fiber optic strands is used as a light delivery source to activate the photopharmaceutical, and hydrogel contact with the fiber optic strands is efficient because at manufacture the hydrogel is cast against, and placed in intimate physical contact with, the fiber optic strands and conforms to the regular geometry of these strands achieving intimate optical coupling. The formation of the hydrogel to skin surface juncture occurs at the point of engagement of the hydrogel to the skin surface. The physical characteristics of the hydrogel necessary to establish intimate skin contact are those described for electrode contact in the prior art references, cited above. Similar characteristics are required for performing PDT with the present invention, with the added hydrogel attributes of light transmission and hydration of the skin.

The mechanical changes hydration produces in the stratum corneum layer have substantial impact on the optical coupling efficiency of externally applied light in the red region of the spectrum. The ultra-structure of the stratum corneum is an array of flattened essentially dead cells which are constantly being shed in a natural process of skin surface renewal. This results in a very uneven, dry, and highly light reflective layer or barrier to light penetration or transmission. Hydration by contact with emollients and oil-based unguents confers an improved surface but the effect is transitory under projected optical illumination schemes that, through surface heating, rapidly degrade the hydration effect by drying out of the target region. Thus though topically applied agents for PDT may briefly induce an optical improvement, it rarely persists through the projected light illumination phase if surface heating occurs during illumination.

This is in marked contrast with the present invention, where the hydrogel remains in place during the light dosage and serves as a hydration agent and photopharmaceutical reservoir or transport means, and conduit and coupling for both light and fluidized agents to the target tissue or dermal treatment site during all phases of photodynamic therapy of a dermal lesion.

It is the object of the present invention to provide a new and improved combination controller and patch for the photodynamic therapy of dermal lesion and which, in the preferred embodiment, permits the patient undergoing photodynamic therapy to control or vary the applied photodynamic therapy for the patient's comfort and to eliminate, or substantially eliminate, patient discomfort and even pain.

SUMMARY OF THE INVENTION

Combination controller and patch for photodynamic therapy of a dermal lesion located at a dermal treatment site on skin including stratum corneum at the site, the controller is optically connected to the patch and the patch includes transparent coupling (e.g. hydrogel) for covering the dermal treatment site and which contains hydration agent and photopharmaceutical, the transparent coupling couples the hydration agent to the stratum corneum to hydrate and soften the stratum corneum to enhance its optical transmissiveness to facilitate the transmission of light therethrough and to enhance its chemical transmissiveness to facilitate the transmission therethrough of the photopharmaceutical to the dermal treatment site for treatment of the dermal lesion, a source of light delivery is included in the patch and receives optical energy from the controller and delivers the light through the transparent coupling and the hydrated stratum corneum to the photopharmaceutical at the site to photoactivate the photopharmaceutical to biologically engage and treat the dermal lesion.

DESCRIPTION OF THE DRAWINGS

FIG. 1 is a diagrammatical illustration, substantially in cross-section, illustrating prior art photodynamic therapy of a dermal lesion using projection optics;

FIG. 2 is a diagrammatical illustration, substantially in cross-section, illustrating a first embodiment of the patch the present invention;

FIG. 2A is a partial cross-sectional view of the cover of the patch of the present invention and which illustrates that the internal surface of the cover may be provided with a suitable light reflecting layer or coating;

FIG. 3 is a perspective cut away diagrammatical illustration of the first embodiment of the patch shown in situ over a dermal treatment site;

FIG. 3A is a partial perspective view of an optical fiber strand illustrating diagrammatically the lateral or radial exiting of laser light;

DETAILED DESCRIPTION OF THE PREFERRED EMBODIMENTS

Figure 4:
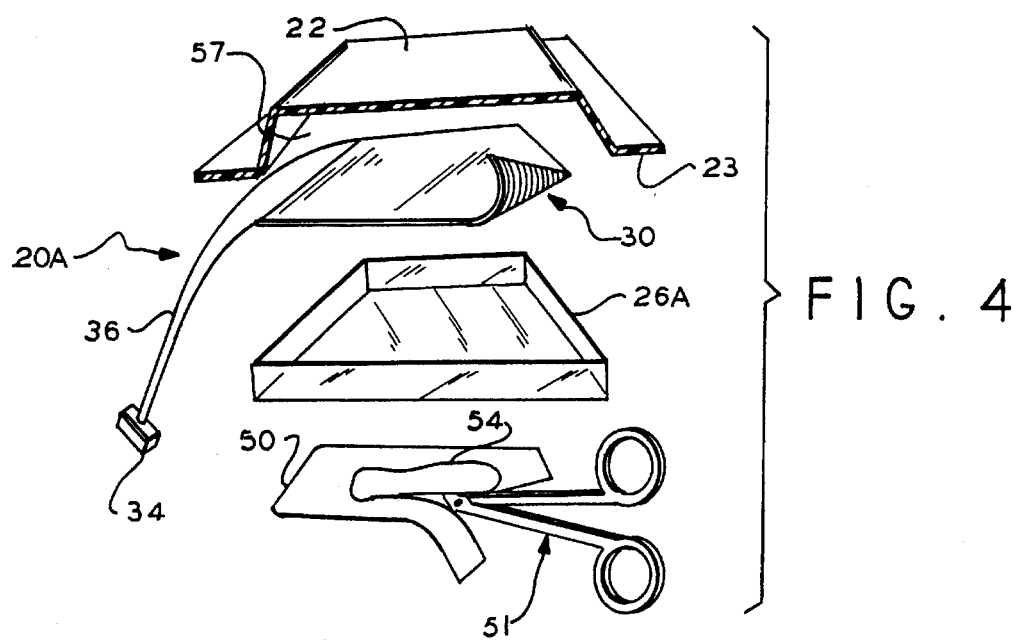
FIG. 4 is an exploded view, partially in cross-section, illustrating a second embodiment of the patch of the present invention.

FIG. 1 illustrates prior art photodynamic therapy of dermal lesions 10 located in a person's skin indicated by general numerical designation 12, which skin includes the stratum corneum 14. [It will be understood that the dermal lesions 10 are illustrated diagrammatically in FIG. 1, and in FIGS. 2, 3 and 5 referred to below, by the darkest spots shown in the skin 12. It will be further generally understood that the dermal lesions 10 are generally located under the stratum corneum 14 or within the skin 12 or can extend partly outwardly of the skin as illustrated in FIG. 1.] Projective light source 13 directs light, indicated by arrows 16, onto the skin 12 and, as noted generally above, the stratum corneum 14 scatters the light with substantial portions of the light, as indicated by arrow 17, being reflected away from the stratum corneum 14 and thereby not initiating any photodynamic therapy. However, as further noted above, red light within the light 16 can penetrate the skin 12 to 3–4 mm. The projective light source 13 is typically either a filtered incandescent source or a laser and is normally arranged to project the light 16 perpendicular to the skin 12 and corneum 14. It will be further understood from FIG. 1 that the dermal treatment site, indicated generally by numerical designation 18, is generally not well defined in distinction to the dermal treatment site produced by the present invention described below and illustrated particularly in FIG. 2.

Figure 7:
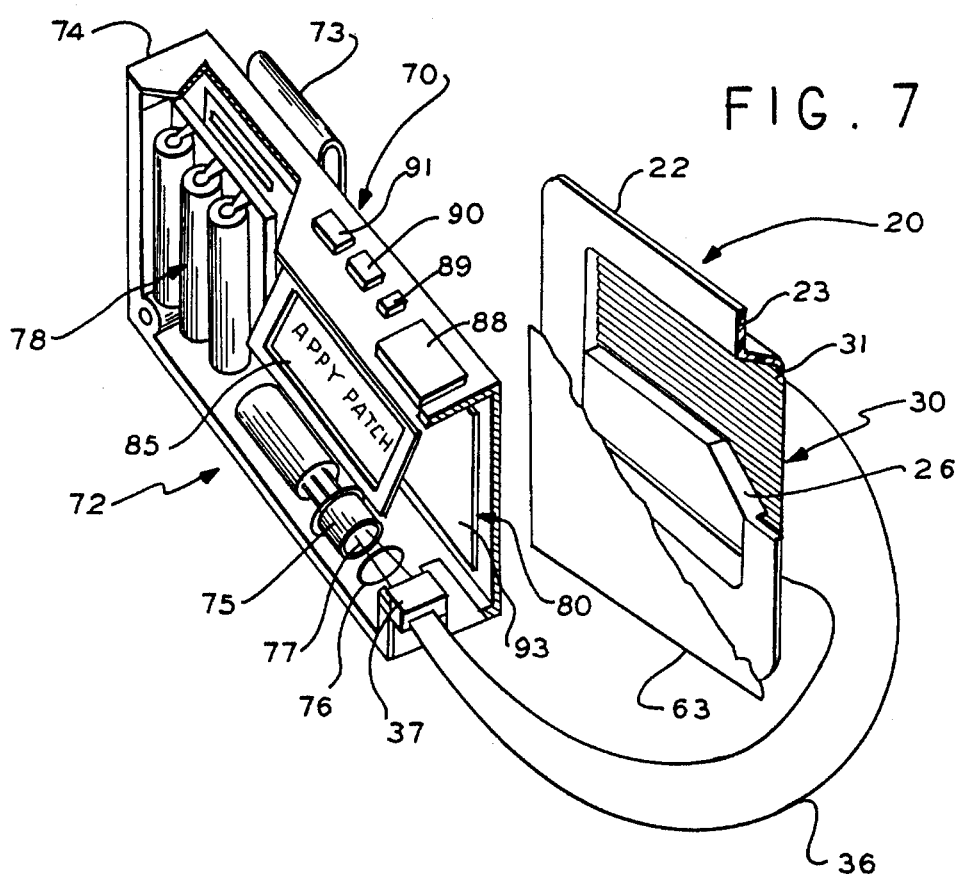
FIG. 7 is a perspective view, in partial cutaway, illustrating an embodiment of the combination controller and patch of the present invention for applying photodynamic therapy to dermal lesions.

Referring to FIG. 2, the first embodiment of a patch of the present invention, particularly useful for use with the controller 80 of the present invention shown in FIG. 7 and described blow, is indicated by general numerical designation 20. Patch 20 includes a cover 22, which may be also referred to as a container, and may be made, for example, of Mylar and suitably formed into the shape shown such as for example by vacuum forming. It will be noted that the lower portion of the cover 22 may be provided with an outwardly extending flange or peripheral portion 23 circumscribing the lower cover portion, and which peripheral portion 23 may be provided with a suitable layer of adhesive 24, of the type known to the art to be compatible with the human skin, for sealingly engaging the skin 12 to seal the cover 22 to the skin and define and cover a dermal treatment site indicated by general numerical designation 25; the flange or peripheral portion 23 and adhesive layer 24 are better seen in FIG. 2A. It will be noted that in use of the patch 20 of the present invention illustrated in FIG. 2, the dermal treatment site 25 is comparatively narrowly and well defined as contrasted to the open and comparatively poorly defined prior art dermal treatment site 18 illustrated in FIG. 1. The cover 22 provides an internal chamber 22A, better seen in FIG. 2A, opposite the dermal treatment site 25 and a body or layer of transparent hydrogel 26 is received and resides within the chamber 25. Transparent hydrogel 26 may be a transparent hydrogel of the type described above and may be, for example, a polyvinyl alcohol having a water matrix which water serves as a hydration agent in the present invention; the water or hydration agent is illustrated diagrammatically in FIG. 2 by circles 27. In addition to containing the water or hydration agent 27, the transparent hydrogel 26 includes a suitable photopharmaceutical for treating the dermal lesion 10 and which photopharmaceutical is illustrated diagrammatically in FIG. 2 by the circles 28; the photopharmaceutical 28 may be introduced into the transparent hydrogel 26 by absorption. The photopharmaceutical 28 may be, for example, photopharmaceutical 5-ALA available from the Sigma Chemical Company, St. Louis, Mo., and which photopharmaceutical is made photoactive by red light at a wavelength of substantially 635 nm.

The patch 20, FIG. 2, further includes a light delivery source indicated by general numerical designation 30 and which may be an optic laser light-emitting panel available from Lasermax, Inc., of Rochester, N.Y. which emits monochromatic red light having a wavelength of substantially 635 nm so as to be photoactively compatible with and matched to the photoactive wavelength of the photopharmaceutical 28 contained in the transparent hydrogel 26. The optic laser light-emitting panel 30 includes a plurality of optical fiber strands 31 indicated in transverse cross-section by the linearly aligned circles shown in FIG. 2 and which strands 31 may be better seen in cylindrical perspective view in FIG. 3. Referring to FIG. 2A, the cover 22 includes an internal surface 34 which may be provided with a suitable layer or coating of reflective material 35 which may be a layer of suitable reflective foil suitably adhesed to the internal surface 34, or thermally staked thereto, or may be a suitable reflective coating provided by a suitable deposition process; reflective layer 35 is not shown in FIG. 2 since it is relatively thin as compared to the cover 22 but it will be understood that such reflective layer is present in patch 20 of FIG. 2. The optic laser light-emitting panel 30 resides within the chamber 25 and may be suitably secured to the cover 22, and to or through the reflective layer 35, by a suitable adhesive or by suitable thermal staking. The transparent hydrogel 26 is a castable hydrogel and is cast into intimate physical and optical contact with the panel 30.

Referring to FIG. 3, it will be understood that the strands of optical fibers 31 of the optic laser light-emitting panel 30 are actually the ends or end portions of the optical fibers contained in the optical fiber bundle 36 which terminate in a suitable optical fiber connector 37; as shown in FIG. 4, the cover 22 is provided with a suitably sized opening 51 for admitting the optical fiber bundle 36 therethrough. Connector 37 is for being connected to a suitable laser diode 40 for producing, in the preferred embodiment, monochromatic red light indicated by the arrows 42 having a wavelength of substantially 635 nm; the laser diode 36 may be, for example, a told 635 available from Toshiba Optical Systems. The laser light 42 is transmitted or ducted to the optical strands 31, through the optical bundle 36 and, as may be understood from FIG. 3A, the optical fiber strands 31 are provided with side openings or lateral notches 39 which cause or permit the laser light 42 (FIG. 3) to be emitted at a number of angles from the sides of the strands 31 but which light is ultimately reflected by the reflective layer or surface 35 (FIG. 2A) and caused to ultimately impinge upon the stratum corneum 15 and skin 12. As may be noted in FIG. 2, the laser light, as indicated by the arrows 29, is reflected off the reflective surface (FIG. 2A) and transmitted through the transparent hydrogel 26.

Upon patch 20, FIGS. 2 and 3, being sealingly engaged to the skin 12 and stratum corneum 14 as illustrated in FIGS. 2 and 3 and described above, the water or hydration agent 27 contained in the transparent hydrogel 26 engages the stratum corneum 14 and immediately begins to hydrate and soften the stratum corneum to enhance its optical transparency or transmissiveness to facilitate the transmission of the laser light 37 therethrough and to enhance its chemical transparency or transmissiveness to facilitate the transmission therethrough of the photopharmaceutical 28 and into the dermal treatment site 25 containing the dermal lesion 10. The laser light 42 (FIG. 3) is introduced into the dermal treatment site 25 and illuminates the site by light diffusion which photoactivates the photopharmaceutical 28 to initiate its biological activity and to cause the photoactivated photopharmaceutical to biologically engage and treat the dermal lesion 10. After such treatment, as noted generally above, the cover 22 of the patch 20 may remain in place after the photodynamic therapy as a temporary protective dressing for the dermal treatment site 25. It will be further understood that a biologically sufficient quantity of photopharmaceutical is introduced into the hydrogel to accomplish treatment of the dermal lesion.

Figure 5:
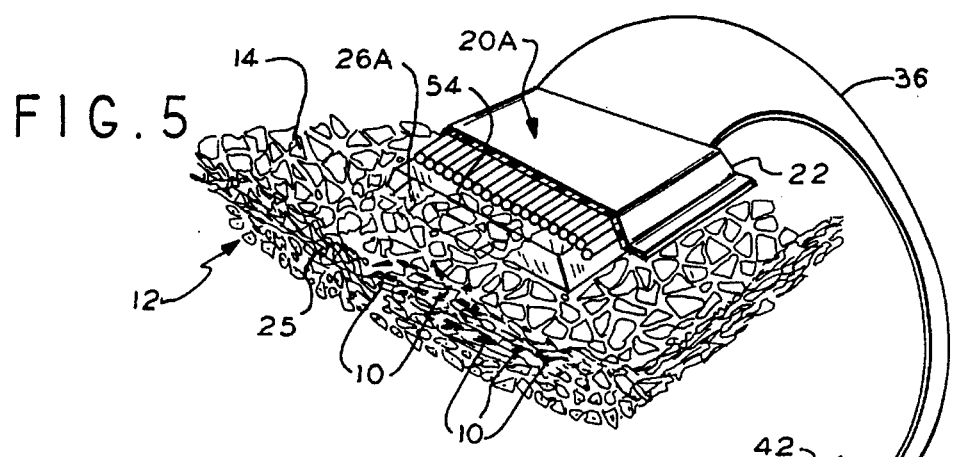
FIG. 5 is a perspective diagrammatical illustration, substantially in cross-section, illustrating the second embodiment of the patch shown in situ over a dermal treatment site and also showing connection to a laser diode.
Figure 6:
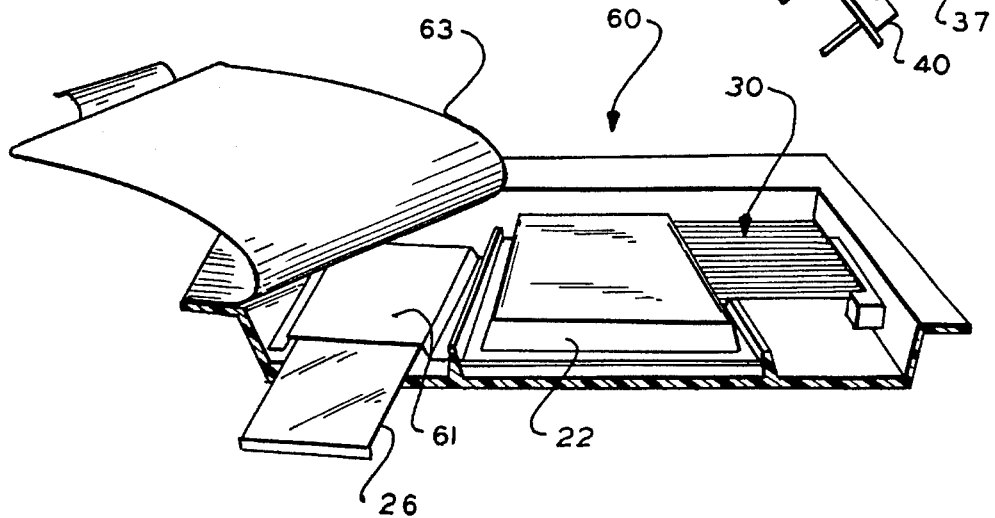
FIG. 6 is a diagrammatical perspective view, partially in cross-section, illustrating a procedure tray containing the components of the first embodiment article of manufacture of the present invention illustrated in FIGS. 2 and 3.

Referring now to FIGS. 4 and 5, a second embodiment of a patch of the present invention, particularly useful in combination with the controller 80 of the present invention shown in FIG. 7 and described below, is shown and indicated by general numerical designation 20A. The structural elements in patch 20A which are the same, or substantially the same, as the corresponding structural elements in patch 20 of FIGS. 2 and 3, are given the same numerical designation as the elements in FIGS. 2 and 3. It will be generally understood that patch 20A applies photodynamic therapy to dermal lesions 10, FIG. 5, in substantially the same manner as patch 20 of FIGS. 2 and 3. However, in the embodiment 20A, the transparent hydrogel 26A while including the water or hydrating agent indicated by circles 27 in FIG. 2, does not contain the photopharmaceutical indicated by circles 28 in FIG. 2. Patch 20A further includes a second layer or sheet of transparent hydrogel 50 which is smaller in size or thickness than transparent hydrogel 26A and which, although containing a water matrix in which the photopharmaceutical is contained, is highly dehydrated as compared to the transparent hydrogel 26A. The relatively highly dehydrated state of the transparent hydrogel 50 permits the transparent hydrogel 50 to be cut and trimmed, such as by a pair of scissors 51, into a body of hydrogel 54 having a size much smaller than the transparent hydrogel 26A and shaped into substantially the same shape as the underlying dermal lesion 10, FIG. 5. As is known, the photopharmaceutical contained in the transparent hydrogel 50 is toxic, typically acidic, and its application to the skin of a patient can be at least somewhat discomforting or even painful. It has been discovered that by reducing the size of the hydrogel containing the photopharmaceutical a reduced but still biologically sufficient quantity of photopharmaceutical can be applied photodynamically to the patient but with reduced discomfort. This also facilitates a photopharmaceutical profile that minimizes the application of the photopharmaceutical to healthy tissue at the dermal treatment site 25, FIG. 5, yet allows the controlled delivery of photoactivating light to the entire dermal treatment site 25. In application, and in practice of the photodynamic therapy, the trimmed hydrogel 54 resides within the cover 22 intermediate the transparent hydrogel 26A and the treatment site 25 as may be noted particularly from FIG. 5. The transparent hydrogel 26A and trimmed hydrogel body 54 function in substantially the same manner as the single layer of transparent hydrogel 26 in patch 20 of FIGS. 2 and 3 to apply photodynamic therapy to the dermal lesion 10.

A procedure tray is indicated by general numerical designation 60. Procedure tray 60 is a single use procedure tray and may be suitably thermoformed from a suitable plastic such as polypropylene; it will be further understood that the patches 20 and 20A of the present invention are also single use patches. The tray is compartmentalized, as shown, to receive, for example, the components or elements comprising the article of manufacture 20 shown in FIGS. 2 and 3. The transparent hydrogel 26 may be received within a moisture impervious foil or laminate pouch 61, the cover 22 and optic laser light emitting panel 30 may be received in compartments as shown also. The procedure tray 60 is sealed against moisture variation by a "peelable" foil sealing panel 63. The sealing panel 28 is removed and the elements or components of the article of manufacture 20 are assembled as illustrated in FIGS. 2 and 3 and thereafter may be applied to the skin as described above and illustrated diagrammatically in FIGS. 2 and 3.

Referring now to FIG. 7, combination controller and patch for applying photodynamic therapy to dermal lesion embodying the present invention is shown with the combination being indicated by general numerical designation 70. Combination 70 includes controller 72 and patch 20 shown in FIGS. 2 and 3 and described above, or in the alternative patch 20A shown in FIGS. 4 and 5 and described above. It will be understood that the controller 72 and patch 20, or 20A, are of a size and weight that they can be conveniently carried by a patient receiving the photodynamic therapy. The controller 72 may be provided with a suitable loop 73 through which a patient's belt may be inserted, or the controller 72 may be provided with a suitable clip (not shown) for clipping the controller to the patient's clothing.

Controller 72 includes a housing 74 which may be made of a suitable plastic suitably shaped into the configuration shown. Mounted to the housing 74 is a source of optical energy 75 which may be, for example, a solid state diode laser of the type noted above and which, in a preferred embodiment, emits monochromatic red light having a wavelength of substantially 635 nm. Suitable collimating optics or lens 76 are mounted to the housing intermediate the diode laser 75 and the patch connector 37 for aligning and directing the optical energy or laser light 77, sometimes referred to as light flux, into the connector 37 and thereby into the bundle of optic fibers 36 and to and out the sides of the optical fiber strands 31 of the panel 30 as described above. It will be understood that the connector 37, as shown in FIGS. 3 and 5 and described above, is disconnectable from the housing 74, and it will be further understood that in the preferred embodiment of the present invention the patch 20 is a single use patch which may be disposed of after use; it will be further understood that the controller 72 is not disposable but instead may be used numerous times with different disposable patches. A power supply 78, which may be a plurality of suitable batteries such as rechargeable batteries, is mounted to a housing 74 to provide power to the solid state laser diode 75 and to the computer or processor indicated by general numerical designation 80.

Figure 8:
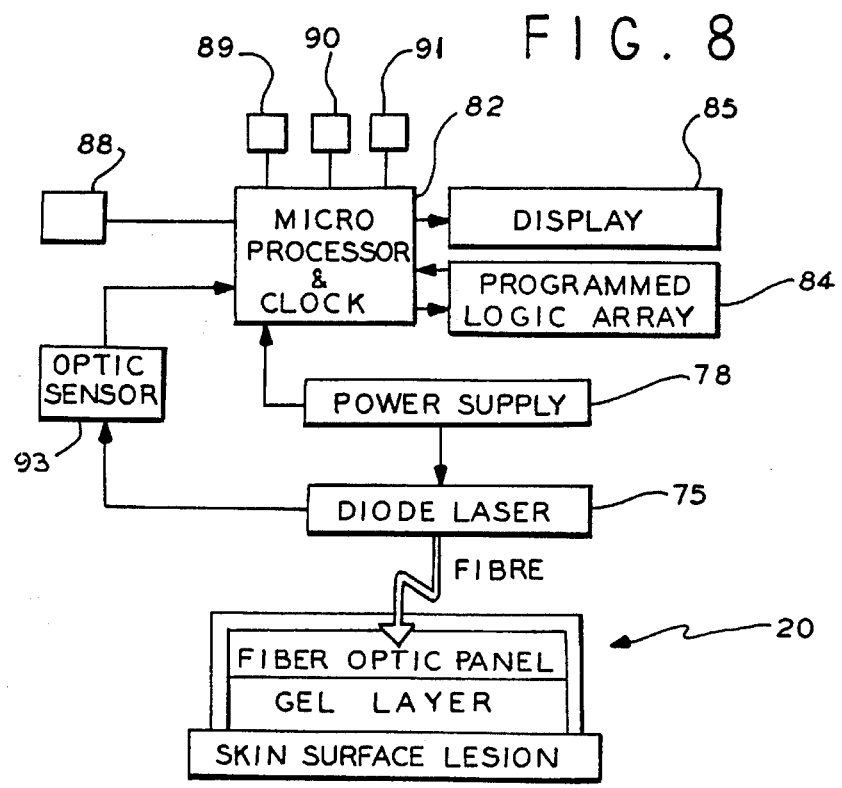
FIG. 8 is a general block diagram of computer means which may be included in the controller of the present invention and a general block diagram of a patch of the present invention.

Computer 80 is suitably mounted in the housing, such as by surface mounting technology of the type known to the art, and includes the microprocessor and clock 82 and program logic array 84 illustrated in block diagram in FIG. 8; these components may be any one of several suitable components known to the art. The power supply 78 also provides power to the computer 80. A suitable liquid crystal display 85, FIG. 7, is suitably mounted to the housing 74 and is connected operably to the microprocessor 82 as indicated diagrammatically in FIG. 8. It will be understood generally that the display 85 provides a visible indication to a patient undergoing photodynamic therapy, or an attending clinician or physician, of the treatment steps of the photodynamic therapy that are being performed or their status. Generally, the patient, attending physician or clinician, operates the controller 72 to apply photodynamic therapy to the patient's dermal lesion through depression of the power-on button 88. If desired, or required, a photodetector 93, may be mounted on the computer 82 and one or more optical fibers from the bundle 36 may be connected to the photodetector whereby the optical energy or laser light applied to the optical fiber strands 31 may be sampled or monitored and suitable input provided from the photodetector to the computer to provide a further control of the optical energy or laser light applied to the patch 20 for photodynamic therapy as described above.

Figure 9:
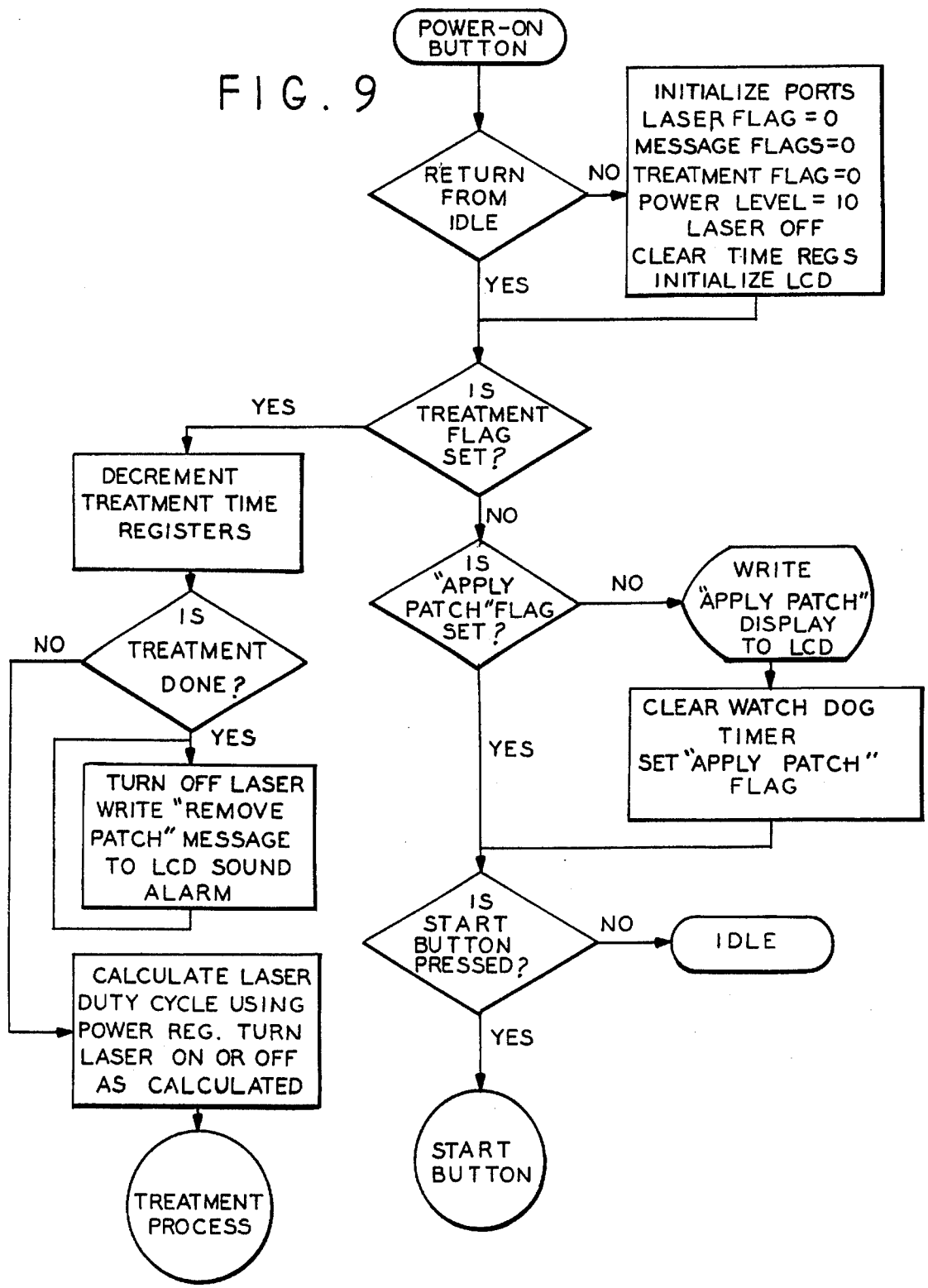
FIG. 9 is a flow chart of the computer program stored in the programmed logic array which is executed without patient, or attending physician or clinician, intervention.
Figure 10:
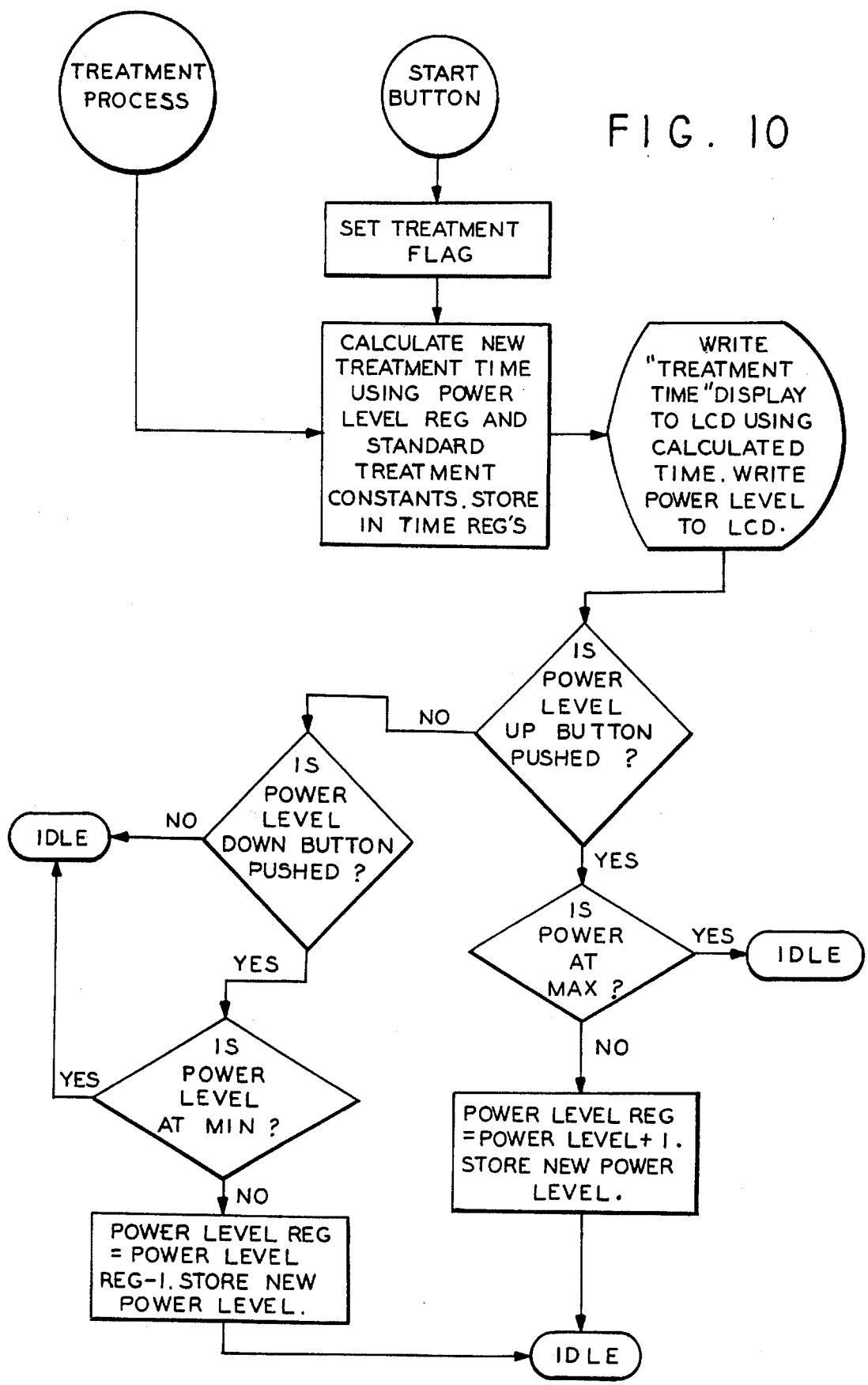
FIG. 10 is a flow chart of the computer program also stored in the program logic array which is executed with patient, or attending physician or clinician, intervention.

Control, and varying of the photodynamic therapy applied to the dermal lesion, may be under the control of the patient receiving the photodynamic therapy or the attending clinician or physician and, more particularly, will be applied generally in accordance with the photodynamic therapy dosage applied to the dermal treatment site pursuant to a preprogrammed time and intensity profile coded into the computer 80 and more particularly as coded into the program logic array 84, FIG. 8, pursuant to the computer program flow charts set forth in FIGS. 9 and 10. It will be understood that the flow charts set forth in FIGS. 9 and 10 will enable a computer programmer of ordinary skill in the art to write and introduce a program into the program logic array 84, in any one of several different computer programming languages, to cause the combination controller and patch of the present invention to apply photodynamic therapy to treat the dermal lesion in accordance with the programmed instructions.

As noted above, photodynamic therapy applied to dermal lesion can cause discomfort and even pain to the patient and it will be further understood, and as noted above with regard to the incorporated publications of Van Gemert et al. and Anderson et al., incorporated hereinabove, that the photodynamic therapy applied can be varied by varying the intensity and/or duration of optical energy or light applied to photoactivate the photopharmaceutical.

Referring again to FIG. 7, it will be noted that the controller 72 includes the above-noted power-on button 88, and a start button 89, a power level up button 90 and a power level down button 91. These buttons are also shown in FIG. 8 as being connected to the microprocessor and clock 82 of the computer 80. Upon the power-on button 88 being depressed, by the patient or an attending physician or clinician, the controller 70 under the control of the computer 80, and pursuant to the program stored in the programmed logic array 84 in accordance with the flow chart set forth in FIG. 9, will apply photodynamic therapy to the patient's dermal lesion as described above with regard to patches 20 and 20A. This program will run automatically in accordance with the dosimetry programmed into the computer in accordance with the predetermined photodynamic treatment protocol determined by the program instructions in the program logic array 84. If the patient experiences discomfort, or even pain, pursuant to the automatically operated photodynamic treatment protocol, the patient, or attending physician or clinician, can intervene by depressing the start button 89, FIGS. 7 and 8, which will cause the computer 80 to apply photodynamic therapy through the patch 20 pursuant to the computer program stored in the program logic array 84 pursuant to the flow chart set forth in FIG. 10. If the patient experiences further discomfort, the patient, or attending physician or clinician, may depress the power level down button 91 to decrease the intensity and/or duration of the optical energy, or laser light, applied to the photopharmaceutical thereby decreasing the photoactivity of the photopharmaceutical and decreasing the patient's discomfort. If the patient is not experiencing discomfort and desires to accelerate the photodynamic therapy of the dermal lesion, the patient, attending physician or clinician, may depress the power level up button 90 whereupon the computer 80, again under the control of the programmed logic array 84 and the instructions programmed therein pursuant to FIG. 10, will increase the intensity of the optical energy, or laser light, applied to the photopharmaceutical to increase its photoactivity until the patient again experiences discomfort whereupon the patient, or attending physician or clinician, may again depress the power level down button to reduce such discomfort.

It will be understood that the term photopharmaceutical as used herein and in the appended claims means an agent which is itself a photosensitizer or which is converted to a photosensitizer in the body.

It will be understood that many variations and modifications may be made in the present invention without departing from the spirit and the scope thereof.

What is claimed is:

1. Apparatus for applying photodynamic therapy to a dermal lesion located at a dermal treatment site on the skin including stratum corneum, comprising:

patch means for applying photodynamic therapy to the dermal lesion and including transparent coupling means containing at least one hydration agent, at least one photopharmaceutical, and optical energy delivery means for delivering optical energy to said patch means, said coupling means for coupling said hydration agent, said photopharmaceutical, and said optical energy to said dermal treatment site;

control means for controlling the photodynamic therapy including a source of optical energy connected to said optical energy delivery means;

said patch means for being secured to said skin over the dermal treatment site to cause said transparent optical coupling means to engage the stratum corneum to cause said hydration agent to hydrate the stratum corneum to enhance its optical transparency to the photopharmaceutical to permit the photopharmaceutical to pass therethrough and enter the treatment site and to enhance the optical transparency of the stratum corneum to facilitate the passage therethrough of said optical energy; and said optical energy delivery means for delivering said optical energy through said transparent coupling means and said hydrated stratum corneum to said photopharmaceutical at the dermal treatment site to photoactivate said photopharmaceutical to cause said photopharmaceutical to biologically engage and treat the dermal lesion.

2. The apparatus according to claim 1 wherein said patch means includes cover means for covering the dermal treatment site provided with sealing means for sealing said cover means over the dermal treatment site, and wherein said transparent coupling means include transparent hydrogel means, including a water matrix, for providing said hydration agent and wherein said photopharmaceutical is absorbed into said water matrix.

3. The apparatus according to claim 2 wherein said cover means includes an internal surface defining a chamber receiving said transparent hydrogel means and wherein said transparent hydrogel means resides in said chamber, and wherein said cover means further comprises a reflective layer provided on said internal surface for reflecting said optical energy through said transparent hydrogel means and to said photopharmaceutical.

4. The apparatus according to claim 2 wherein said source of optical energy is a laser providing laser light; wherein said optical energy delivery means comprise an array of parallel optical fibers for emitting said laser light from sides thereof, wherein said cover means is provided with an internal reflective surface for reflecting said laser light through said transparent coupling means, and said hydrated stratum corneum into the dermal treatment site, and wherein said transparent hydrogel means is comprised of castable transparent hydrogel and wherein said hydrogel is cast into intimate physical and optical engagement with said array of parallel optical fibers.

5. The apparatus according to claim 4 wherein said photopharmaceutical is photoactivateable at a predetermined wavelength and wherein said laser provides monochromatic light at said predetermined wavelength through said array of parallel optical fibers.

6. The apparatus according to claim 5 wherein said laser provides said monochromatic light at a wavelength of 635 nm.

7. The apparatus according to claim 4 wherein said transparent hydrogel means comprise a first layer of hydrogel received in said chamber and a second layer of hydrogel received in said chamber and for residing intermediate said first layer of hydrogel and the dermal treatment site, said first layer of hydrogel including a water matrix providing said hydration agent and said second layer of hydrogel being smaller in size than said first layer and generally shaped to cover only the dermal lesion located at the dermal treatment site, and said second layer of hydrogel including a water matrix into which said photopharmaceutical is absorbed.

8. The apparatus according to claim 2 wherein said sealing means comprises a lower portion provided on said cover means which lower portion includes an outwardly extending peripheral portion circumscribing said lower portion and a layer of adhesive applied to said peripheral portion for sealingly engaging the skin to seal said cover means to the skin over the dermal treatment site.

9. The apparatus according to claim 1 wherein said control means includes a power supply for providing power to said source of optical energy, wherein said control means includes computer means including a programmed logic array under the control of a patient receiving the photodynamic therapy, said computer means connected to said power supply to permit said patient to control the amount of power supplied to said laser and the time said power supply supplies power to said laser to thereby permit the patient to control and vary the photodynamic therapy applied to the dermal lesion.

* * * * *